United States Patent [19]

Munir

[11] Patent Number: 4,640,894

[45] Date of Patent: Feb. 3, 1987

[54] PRODUCTION OF ISOMALTULOSE USING IMMOBILIZED MICROORGANISMS

[75] Inventor: Mohammad Munir, Obrigheim, Fed. Rep. of Germany

[73] Assignee: Suddeutsche Zucker-Aktiengesellschaft, Mannheim, Fed. Rep. of Germany

[21] Appl. No.: 793,005

[22] Filed: Oct. 30, 1985

Related U.S. Application Data

[63] Continuation of Ser. No. 290,083, Aug. 4, 1981, abandoned.

[30] Foreign Application Priority Data

Oct. 9, 1980 [DE] Fed. Rep. of Germany ....... 3038219

[51] Int. Cl.⁴ .................. C12P 19/12; C12N 11/02; C12N 11/10; C12N 11/12
[52] U.S. Cl. ..................... 435/100; 435/97; 435/177; 435/178; 435/179; 435/180; 435/182
[58] Field of Search ............. 435/94, 100, 174, 177, 435/178, 179, 180, 182, 233, 97

[56] References Cited

U.S. PATENT DOCUMENTS

| | | | |
|---|---|---|---|
| 3,974,036 | 8/1976 | Snell | 435/94 X |
| 4,167,447 | 9/1979 | Masri et al. | 435/178 |
| 4,208,482 | 6/1980 | Ehrenthal et al. | 435/94 X |
| 4,251,632 | 2/1981 | Chen et al. | 435/233 X |
| 4,359,531 | 11/1982 | Bucke et al. | 435/97 |

FOREIGN PATENT DOCUMENTS 1099 3/1979 European Pat. Off. .
2063268 6/1981 United Kingdom .

OTHER PUBLICATIONS

Chibata, et al., Advances in Applied Microbiology, vol. XXII, 1977, pp. 1–9.

*Primary Examiner*—David M. Naff
*Attorney, Agent, or Firm*—Armstrong, Nikaido, Marmelstein & Kubovcik

[57] ABSTRACT

Isomaltulose (6-0-alpha-D-glucopyranosido-D-fructose) is produced by passing a pure sucrose solution through a reactor containing dead, immobilized cells of an isomaltulose-forming microorganism. The sucrose solution preferably contains 45 to 75% by weight sucrose and has a temperature of 45° to 65° C.

10 Claims, No Drawings

PRODUCTION OF ISOMALTULOSE USING IMMOBILIZED MICROORGANISMS

This is a continuation of application Ser. No. 290,083 filed Aug. 4, 1981, and now abandoned.

BACKGROUND OF THE INVENTION

1. Field of the Invention

This invention relates to the preparation of isomaltulose and, more particularly, to the preparation of isomaltulose from sucrose.

2. Description of the Prior Art

Isomaltulose is an intermediate product for the preparation of glucopyranosido-1,6-mannitol (German Auslegeschrift No. 2 520 173) and glucopyranosido-1,6-sorbitol (isomaltitol, German Pat. No. 2 217 628). Both substances may be used as sugar substitutes.

German Pat. No. 1 049 800 discloses that sucrose is enzymatically converted into isomaltulose. The enzymes are of microbial origin. Besides Protaminobacter rubrum, other bacteria such as Erwinia carotovora, Serratia marcescens, Serratia plymuthica and Leuconostoc mesenteroides are capable of this rearrangement (S. Schmidt-Berg-Lorenz, W. Mauch, ZEITSCHRIFT FUER DIE ZUCKERINDUSTRIE, 14, 625–627, [1964]; F. H. Stodola, 126th Meeting of Amer. Chem. Soc., Sept., 1954, Abstracts of papers, p. 5D; W. Mauch, S. Schmidt-Berg-Lorenz, ZEITSCHRIFT FUER DIE ZUCKERINDUSTRIE, 14, 309–315 and 375–383 [1964]).

German Pat. No. 2 217 628 further discloses that the enzymatic conversion of sucrose into isomaltulose can be carried out continuously or batch-wise in a 15 to 40% solution with strong stirring and under aerobic conditions at 20° to 37° C.

Moreover, German Offenlegungsschrift No. 2 806 216 discloses how to carry out continuously the culture of isomaltulose-forming microorganisms with simultaneous conversion of sucrose into isomaltulose.

The above-cited known processes suffer from disadvantages, such as:

(a) the living and multiplying cultures of cells consume i.e., oxidize part of the added sucrose for their own living activity (growth and multiplication), so that this part of the sucrose is no longer available for the isomaltulose conversion;

(b) the conversion of the sucrose into isomaltulose and the simultaneous cell multiplication require fermentation with strong agitation and aeration which, in turn, cause high energy consumption;

(c) the concentration of the nutrient substrate of 25% (German Offenlegungsschrift No. 2 806 216) or of 15 to 40% (German Pat. No. 2 217 628) is insufficient for the subsequent production of isomaltulose by direct crystallization (the converted sucrose solution following separation of the cell substance must first be concentrated by evaporation before it can be subjected to crystallization; thus, from 100 kg of converted sucrose solution according to German Offenlegungsschrift No. 2 806 216, about 67 kg of water must be evaporated before isomaltulose crystallizes out);

(d) the multiplication of the cell substance requires not only a suitable carbon source, but also nitrogen salts and nutrient salts (in the above-cited process, the addition of nitrogen and nutrient salts takes place by using sugar solutions of lower purity, such as obtained in sugar mills, in lieu of pure sucrose solutions; these impurities [non-sugars], on one hand, are absolutely necessary for cell growth but, on the other hand, cause loss of isomaltulose during the crystallization due to molasses formation).

The above-cited disadvantages can be avoided in principle provided that it be possible to separate the conversion of sucrose into isomaltulose from the cell multiplication and to stabilize it over a substantial length of time.

It is an object of the present invention, therefore, to provide a continuous conversion of sucrose into isomaltulose (palatinose, 6-O-α-D-glucopyranosido-D-fructose) which avoids the disadvantages discussed above.

SUMMARY OF THE INVENTION

It has now been surprisingly discovered that it is possible to convert the sucrose from pure sucrose solutions into isomaltulose by means of immobilized cells of isomaltulose-forming microorganisms. It could not be expected that isomaltulose-forming microorganisms, for instance, Protaminobacter rubrum (CBS 574.77) in the dead state are capable of converting pure sucrose solutions of high concentration to isomaltulose and of producing isomaltulose of high purity in the process.

DESCRIPTION OF PREFERRED EMBODIMENTS

The process of the invention may be carried out by continuously passing sucrose solutions in concentrations of 45 to 75% by weight, preferably 65 to 75% by weight, and at a temperature of 45° to 65° C. through a reactor filled with immobilized cells and by obtaining the isomaltulose so generated in crystalline form by methods known in the art.

The conversion of the sucrose solution by means of the immobilized cells can be carried out in the reactor either continuously or batch-wise.

As the immobilized cells for producing isomaltulose from sucrose according to the process of the present invention, there may be employed immobilized cells of microorganisms capable of enzymatically converting sucrose into isomaltulose. These include Protaminobacter rubrum (CBS 574.77), Serratia plymuthica (ATCC 15928), Serratia marcescens (NCIB 8285) and leuconostoc mesenteroides (NRRL B-512 F [ATCC 10830a]). Immobilized cells of Protaminobacter rubrum (CBS 574.77) are preferably employed.

To produce the cells which then must be immobilized for the process of the invention, an optimal cell multiplication takes place in a nutrient medium containing only 5% by weight of dry substance content. The nutrient medium contains a syrup (an intermediate product of the sugar industry), "corn steep liquor" and $(NH_4)_2HPO_4$. However, using a substantially more economical nutrient substrate consisting only of sugar beet molasses and $(NH_4)_2HPO_4$ is advantageous. To prepare this nutrient substrate, the molasses is diluted with distilled water to a content of 5% by weight of dry substance. 0.1 kg of $(NH_4)_2HPO_4$ are added as an additional source of nitrogen and phosphate to 100 kg of this solution. The pH value is adjusted to 7.2 by means of caustic soda or caustic potash or with hydrochloric acid.

The inoculum of an isomaltulose-forming microorganism, for instance, Protaminobacter rubrum (CBS 574.77) is transferred with 10 ml of sterile nutrient substrate of the above composition to a shake-flask and incubated in 200 ml of the same nutrient medium at 29°

C. As soon as the cell count in the agitated culture reaches $5 \times 10^9$ cells/ml, the culture is transferred into a small fermenter together with nutrient medium of the above composition and is made to multiply at the maximum possible aeration and stirring rate at 29° C. The multiplication is controlled in the same manner as for the agitation culture by the determination of the cell count. As soon as the cell count reaches $5 \times 10^9$ germs/ml, the fermenter can be harvested.

Basically all the methods cited by I. CHIBATA (Immobilized enzymes, John Wiley and Sons, New York, London, 1978) for immobilizing entire cells are suited to immobilize the cells generated. The methods which were found to be specially applicable include flocculation with a cationic flocculent; flocculation with chitosan; inclusion into a calcium alginate matrix, inclusion into cellulose diacetate or cellulose triacetate; inclusion into a K-carrageenan gel; and a flocculation with a cationic flocculent or an anionic flocculent or a combination of both of these. These methods are illustrated in greater detail as follows:

(a) The contents of the fermenting vessel are reacted in that vessel itself or in another with a 1% solution of a cationic flocculent; the required amount of flocculent solution must be ascertained in preliminary tests; the flocculated cell substance is allowed to settle, the excess liquid is decanted off, the precipitate is washed twice with phosphate buffer (0.1M, pH=7.0); thereupon, the cell substance is dewatered to give an extrudable paste, extruded into strands, dried, ground and sifted.

(b) While stirring slowly, a 0.2% chitosan solution in an amount of 0.5 to 2.0 liters is added slowly to 10 l of fermenter beer; the flocculated cell substance is washed with phosphate buffer (0.1M, pH=7.0), dewatered in a centrifuge, for instance, a beaker or a full-casing centrifuge, extruded into strands, dried, ground and sifted.

(c) The cell substance is separated in a centrifuge from the fermenter beer; 5 to 20 g of this cell suspension (dry substance content is about 10%) are suspended in 45 to 60 ml of sodium alginate solution (8 g in 100 ml) and are pressed through a cannula (0.55 mm diameter) into a 2% CaCl$_2$ solution; the beads so produced are stirred for about another 15 minutes in the CaCl$_2$ solution and then rinsed with water; then the beads are dried at room temperature for about 20 hrs.

(d) The cell substance is separated from the fermenter beer in a centrifuge, washed with phosphate buffer (0.1M, pH=7.0) and lyophilized. 15 g of cellulose diacetate are dissolved under reflux in 100 ml of a mixture of dimethylsulfoxide and acetone (6:4) at 90° C.; and cooled to 30° C., 3 to 30 g of lyophilized cells are added; this suspension is pressed through a cannula (0.8 mm) into water at room temperature; the beads formed are dried.

(e) The cell substance is separated in a centrifuge from the fermenter beer; 5 g of this cell substance are suspende in 5 ml of physiological saline at 45° to 50° C.; 1.7 g of K-carrageenan (soluble polysaccharide sulfuric ester) are dissolved in 34 ml of physiological saline at 45° to 60° C.; both solutions are mixed and kept at 10° C. for 30 minutes; the gel so obtained is hardened in a cold, 0.3 molar KCl solution and is then broken up in pieces about 3 mm in size.

(f) The fermenter beer is reacted either in the fermenter itself or in another vessel first with a 1% solution of a cationic flocculent and then with a 1% solution of an anionic flocculant; the required amount of flocculant must be ascertained by preliminary tests; the flocculated cell substance is allowed to settle, washed with phosphate buffer (0.1M, pH=7.0), extruded into strands, dried, ground and sifted.

To prevent leakage of the cells, the preparations made by the above methods require cross-linking. Bifunctional reagents are used for cross-linking, for instance, glutaraldehyde. It is not possible to use the conventionally employed glutaraldehyde concentration of 2.5 to 5% for a contact time of 30 to 45 minutes as regards isomaltulose-forming microorganisms. It was found that under these conditions all the immobilized preparations were wholly inactivated. The optimal cross-linking conditions for the present method were found to be a concentration of 0.1% of glutaraldehyde and a treatment time of 10 minutes.

The cells immobilized and cross-linked by one of the above-cited methods may be placed into a suitable column reactor. This reactor must be heatable and be of a diameter-to-bed height ratio of 1:1 to 1:20, preferably 1:1 to 1:10, in particular, 1:1.5 to 1:5. A pure sucrose solution (65 to 75% by weight) is pumped at a temperature of 40° to 60° C., either from top to bottom or from the bottom to the top of the column. The flow rate is so adjusted that a contact time of 1 to 10 hours, preferably 4 to 7 hours, is obtained (corresponding to 0.2–0.8 g of sucrose, preferably 0.4–0.6 g of sucrose per gram of [dry] immobilized cells per hour). The sucrose used is fully converted and about 1% glucose, 4% fructose, 82% isomaltulose and 13% of 1-O-α-D-glucopyranosido-D-fructose are obtained.

Part of the isomaltulose can be obtained in crystalline form merely by cooling the solution. Another amount of isomaltulose can be crystallized out of the mother liquor by evaporating and cooling whereby a total of about 91.5% of the isomaltulose can be obtained in crystalline form.

The process can be advantageously implemented in such a manner that the sucrose solution is made to pass at a higher rate through the column, whereby only 75 to 80% of the sucrose is converted. Part of the isomaltulose can be crystallized out of the product flow by cooling and the balance, after being replenished with fresh sucrose solution, can be made to pass once more through the column. The advantage of this operation is that, because of shorter contact time, the formation of the 1-O-α-D-glucopyranosido-D-fructose is suppressed. As an end result, a larger yield of the desired isomaltulose is achieved.

The advantages of the process of the invention are:

(a) the isomaltulose-containing solution can be made to crystallize directly without prior concentration, whereby substantial economies in energy are obtained;

(b) the use of dead cells increases the isomaltulose yield since sucrose is no longer required for the metabolism of the bacterial substance;

(c) the isomaltulose yield is increased again by the possibility of employing pure sucrose solutions and hence avoiding the formation of molasses;

(d) because sucrose solutions with concentrations in excess of 65% are microbiologically stable, the substrate need no longer be sterilized;

(e) another, non-negligible advantage is that, due to the higher substrate concentration, lesser volumes need be treated. Hence, more compact apparatus can be used;

(f) the multiplication of the bacterial substance to produce immobilized cells can take place under optimized growth conditions. Accordingly, a compromise between optimal conditions for conversion into isomaltulose and for the growth of bacteria is no longer required;

(g) an economical nutrient substrate, for instance, diluted molasses solutions, can be used for preparing the bacterial substance.

The procedure of the process is explained below in closer detail in relation to two examples.

EXAMPLE 1

(a) Cells from an inoculum of the Protaminobacter rubrum strain (CBS 574.77) are transferred with 10 ml of a sterile nutrient substrate consisting of 8 kg of thick juice from a sugar plant (dry substance content=65%), 2 kg of corn steep liquor, 0.1 kg of $(NH_4)_2HPO_4$ and 89.9 kg of distilled water (adjusted, if needed, to a pH of 7.2). This suspension is used as the inoculating material for the shaker-machine pre-culture in 1-liter flasks with 200 ml each of the nutrient solution of the above composition. 20 such flasks (total contents, 4 liters) are inoculated at 29° C. for 30 hours.

16 l of nutrient solution of the above composition are inoculated in a 30 l small fermenter with the contents of the above 20 flasks (4 liter) and fermented at 29° C. at an aeration rate of 20 l/min and a stirring rate of 350 rpm. The increasing cell count is determined with a microscope. When a concentration of $5 \times 10^9$ cells/ml is reached, the contents of the fermenter are transferred to another container and reacted therein with a cationic flocculant (for instance, PRIMAFLOC C 7 by Rohm & Haas, Philadelphia, Pa., USA). The flocculated cells are allowed to settle, decanted washed with 0.1M phosphate buffer of a pH of 7.0 and dewatered in the centrifuge. Then the substance is extruded into strands, air-dried and ground.

(b) The 0.3 to 0.8 mm sifted fraction from the aboveobtained preparation is stirred in a 0.1% glutaraldehyde solution for 10 minutes, washed with a phosphate buffer (0.1M, pH=7.0) and filled under water into a heatable column. The column is then heated to 50° C. and a 70% sucrose solution is pumped continuously through this column. The flow rate is adjusted in such a manner that no sucrose can be detected anymore at the end of the column. The isomaltulose solution so obtained is fed into a cooling crystallizer, cooled to 20° C., and the crystallized isomaltulose is separated from the mother liquor in wire-basket centrifuges.

EXAMPLE 2

Cells from an inoculum of the Protaminobacter rubrum strain (CBS 574.77) are suspended in 10 ml of a sterile nutrient substrate consisting of 6.25 kg of sugar beet molasses (dry substance content=80%), 0.1 kg of $(NH_4)_2HPO_4$ and 93.65 kg of distilled water (adjusted to a pH of 7.2 with HCl if necessary). This suspension is used as the inoculating material for the shaker machine pre-culture in 1 liter flasks with 200 ml each of the nutrient solution of the above composition. 20 such flasks (total contents 4 liters) are incubated for 30 hours at 29° C. 16 l of the nutrient solution of the above composition are inoculated in a 30 l small fermenter with the contents of the above 20 flasks and are fermented at 29° C. with an aeration rate of 20 l/min and a stirrer speed of 350 rpm.

The procedure continues as described in EXAMPLE 1a and 1b.

Although the invention has been described in conjunction with certain preferred embodiments, it is not intended to be limited thereto, but instead includes all those embodiments within the spirit and scope of the appended claims.

What is claimed is:

1. A process for producing isomaltulose by enzymatic conversion of sucrose using dead immobilized cells of an isomaltulose-forming microorganism comprising continuously passing a pure sucrose solution having a concentration of from 45 to 75% by weight sucrose at a temperature of about 45° to 65° C. through a reactor filled with said dead, immobilized cells of an isomaltulose-forming microorganism so that the sucrose is converted to a product containing primarily isomaltulose.

2. A process for producing isomaltulose by enzymatic conversion of sucrose using dead, immobilized cells of an isomaltulose-forming microorganism comprising continuously passing a pure sucrose solution having a concentration of from 65 to 75% by weight sucrose at a temperature of about 45° to 65° C. through a reactor filled with said dead, immobilized cells of an isomaltulose-forming microorganism so that the sucrose is converted to a product containing primarily isomaltulose.

3. Process according to claim 1 or 2, wherein the microorganism is *Protaminobacter rubrum* (CBS 574.77), *Serratia plymuthica* (ATCC 15928), *Serratia marcescens* (NCIB 8285) or *Leuconostoc mesenteroides* (NRRL B-512F).

4. Process according to claim 3, wherein the immobilized cells are cross-linked with glutaraldehyde or a cyanuric halide.

5. Process according to claim 3, wherein the cells are immobilized by flocculation with a cationic flocculating agent.

6. Process according to claim 3, wherein the cells are immobilized by flocculation with chitosan.

7. Process according to claim 3, wherein the cells are immobilized by inclusion in a calcium alginate matrix.

8. Process according to claim 3, wherein the cells are immobilized by inclusion in cellulose diacetate or cellulose triacetate.

9. Process according to claim 3, wherein the cells are immobilized by inclusion in K-carrageenan gel.

10. Process according to claim 3, wherein the cells are immobilized by flocculation with a cationic or anionic flocculating agent or with a combination of the two.

* * * * *